「United States Patent」 (12)
Mattson

(10) Patent No.: US 6,500,611 B2
(45) Date of Patent: Dec. 31, 2002

(54) INVIABLE VIRUS PARTICLES AS SCAFFOLDS FOR CONSTRUCTING FLEXIBLE DETECTION SYSTEMS

(76) Inventor: Thomas L. Mattson, 20220 Tidewind Way, Germantown, MD (US) 20874

( * ) Notice: Subject to any disclaimer, the term of this patent is extended or adjusted under 35 U.S.C. 154(b) by 0 days.

(21) Appl. No.: 09/931,094

(22) Filed: Aug. 17, 2001

(65) Prior Publication Data

US 2002/0025515 A1 Feb. 28, 2002

Related U.S. Application Data

(60) Provisional application No. 60/225,741, filed on Aug. 17, 2000.

(51) Int. Cl.[7] ............................. C12Q 1/70; A61K 39/12
(52) U.S. Cl. ......................... 435/5; 435/7.94; 435/7.8; 435/471; 435/472; 435/475; 424/204.1; 424/205.1
(58) Field of Search ..................... 435/5, 7.94, 7.8, 435/471, 472, 475; 424/204.1, 205.1

(56) References Cited

U.S. PATENT DOCUMENTS 5,861,282 A * 1/1999 Aldovini et al. ........... 435/69.3

FOREIGN PATENT DOCUMENTS

IT WO 98/53100 * 11/1998

OTHER PUBLICATIONS

Griep, et al., Fluobodies: green fluorescent single-chain Fv fusion proteins, Journal of Immunological Methods, 1999, 230:121–130.*

Jiang et al., Display of a PorA Peptide from *Neisseria meningitidis* on the Bacteriophage T4 Capsid Surface, Infection and Immunity, Nov. 1997, 65(11):4770–4777.*

* cited by examiner

Primary Examiner—Hankyel T. Park
Assistant Examiner—Stacy S. Brown
(74) Attorney, Agent, or Firm—Foley & Lardner

(57) ABSTRACT

An innovative detection system for detecting small numbers of target analytes is disclosed. This system provides a novel method for attaching multiple copies of reporter groups to a single site on an analyte of interest. This system preferably comprises a virus capsid enclosing multiple detectable reporter groups, and a linking molecule which is capable of linking the capsid to the analyte of interest.

34 Claims, No Drawings

INVIABLE VIRUS PARTICLES AS SCAFFOLDS FOR CONSTRUCTING FLEXIBLE DETECTION SYSTEMS

This application claims the benefit of Ser. No. 60/225,741, filed Aug. 17, 2000.

FIELD OF THE INVENTION

This invention is directed to a novel detection system for detecting small numbers of analytes, and a method for making said detection system.

BACKGROUND

The need for the detection of smaller amounts of target analytes requires the development of more sensitive detection systems. The most widely employed approach solves this problem simply by increasing the number of target analytes, for example, the PCR-like approach. A second general approach is to develop more sensitive methods for detecting limited numbers of target analytes. An example using this approach is the bead-based fiber-optical arrays. See Walt, D. R. (2000), Science 287:451–452. A third general approach involves attaching a larger number of commonly used reporter groups to each target analyte. Since an analyte of interest may offer only a limited number of sites for attaching reporter groups, this third approach is limited by the number of independently available attachment sites, unless multiple reporter groups can be attached to each attachment site. Numerous methods applying this third approach have been reported. For example, multiple reporters may be attached to single attachment sites either by creating a branched structure on the attachment site and then attaching reporter molecules to the distal ends of the created branches, or by bundling the reporter groups together and then attaching the bundle to the individual attachment sites of an analyte of interest.

One example of a commercial technology using the third approach is the Quantigene system. This system uses branched DNA (bDNA) technology to detect target RNA molecules.

Another commercially available method using the third approach involves microspheres, which are small polystyrene particles enclosing multiple reporter groups. The microspheres are often covered with functional groups, thereby enabling the microspheres to be attached to particular targets. For instance, Molecular Probes (Eugene, Oreg.) produces polystyrene microspheres with diameters of as small as 20 nm. The 20 nm microspheres produced by Molecular Probes are reported to contain about 200 equivalents of fluorescein, and can be visualized as single particles in light microscopes, appearing as point sources of fluorescence. See Molecular Probes: Handbook of Fluorescent Probes and Research Chemicals, Sixth Edition, page 111. However, it is generally recognized that polystyrene microspheres are not generally useful for detecting small numbers of target analytes because they tend to be too sticky, and often generate a high, nonspecific background signal.

Alternative methods and approaches for bundling reporter groups would provide new approaches for efforts to reduce nonspecific background binding to levels which would allow detection of fewer analytes than is possible with currently available reporter bundles. Thus, novel methods for bundling could be the central elements in detection systems which are capable of detecting smaller numbers of analytes of interest.

This disclosure provides a new approach for creating a detection system which is capable of linking multiple copies of reporter groups to virtually any target analyte of interest. In this disclosure, a viral particle, preferably a bacteriophage particle, more preferably a Bacteriophage T4 capsid, is used as a scaffold or container to bundle multiple copies of reporter groups.

Various molecules have been incorporated into a viral particle for different purposes, and individual virus particles have been stained with various agents and visualized in light microscopes. For example, see U.S. Pat. No. 5,403,484 and Matsumato, S., Morikawa, K. and Yanagida, M. (1981), J. Mol. Biol. 152:501–516. See also Doolittle, M. M., Cooney, J. J. and Caldwell, D. E. (1996), J. Ind. Microbiol. 16(6): 331–341. However, these previous uses of viral particles either rely on the infectiousness of the virus, or have a limited capability to detect a broad range of analytes of interest.

In contrast, a prominent feature of the presently described detection system is that it can detect almost any analyte of interest by incorporating multiple copies of reporter groups and a linking molecule into a non-infectious viral particle. A major practical advantage of a detection system thus formed is that it provides a simple, fast method for the detection of small numbers of analytes. It is especially true when the nature of the target analytes is such that they cannot be amplified and/or if they offer only a single or a few sites for attaching reporter groups.

SUMMARY OF THE INVENTION

Thus, it is an object of the invention to provide a detection system that is capable of detecting a small number of analytes of interest, and to provide a method for making such a detection system.

In achieving this object, there has been provided, in accordance with one aspect of the present invention, a detection system capable of binding to an analyte, wherein the detection system comprises a non-infectious viral particle, a reporter group linked to the viral particle, and a linking molecule which is capable of linking the viral particle to the analyte; and wherein the reporter group and the linking molecule are not components of a naturally occurring virus.

In one embodiment, the viral particle is a bacteriophage particle, preferably a bacteriophage of the T Even family, and more preferably a Bacteriophage T4.

In a preferred embodiment, the bacteriophage particle comprises a capsid and does not have a tail structure. More preferably, the capsid is a Bacteriophage T4 capsid.

In another embodiment, the detection system of the present invention comprises at least 50 reporter groups, preferably at least 100 reporter groups, and more preferably at least 200 reporter groups.

In yet another embodiment, the reporter group comprises a fluorescent molecule, which preferably comprises a fluorescent protein, such as a green fluorescent protein. The fluorescent protein may preferably be enclosed within a Bacteriophage T4 capsid.

In yet another aspect of the present invention, the reporter group comprises an outer capsid protein covalently linked to a fluorescent protein. Preferably, the outer capsid protein is a non-essential outer capsid protein.

In a preferred embodiment, the linking molecule comprises an outer capsid protein covalently linked to an extra amino acid sequence. The outer capsid protein preferably is a non-essential outer capsid protein, such as the hoc and soc proteins of Bacteriophage T4. The extra amino acid sequence preferably comprises a polypeptide selected from the group consisting of a single chain Fv molecule, an Annexin and a DNA methyltransferase.

In another embodiment, the detection system comprises at least two bacteriophage particles which are linked together, either covalently or non-covalently, which thereby permits an increased number of reporter groups to bind to a single analyte.

A detection system has also been provided, in accordance with one aspect of the present invention, wherein said detection system comprises a viral particle, a fluorescent protein which is enclosed within the viral particle, and a linking molecule which is capable of linking the viral particle to the analyte; and wherein the linking molecule is not a component of a naturally occurring virus.

In another aspect of the present invention, the detection system comprises a viral particle, a reporter group which is linked to the viral particle and comprises a first outer capsid protein covalently linked to a first extra amino acid sequence, and a linking molecule which is capable of linking the viral particle to the analyte and comprises a second outer capsid protein covalently linked to a second extra amino acid sequence; and wherein the first and second extra amino acid sequence are not identical.

There has been provided, in accordance with another aspect of the present invention, a method making a detection system, comprising the steps of:

(1) providing a viral particle;
(2) providing a reporter group comprising a first outer capsid protein;
(3) linking the reporter group to the viral particle;
(4) providing a linking molecule which is capable of linking the viral particle to the analyte and comprises a second outer capsid protein; and
(5) linking the linking molecule to the viral particle; wherein the reporter group and the linking molecule are not components of a naturally occurring virus; and wherein either the reporter group or the linking molecule, or both, are exogenous to the viral particle.

In a preferred embodiment, either the step (3) or the step (5), or both, of the above method are not performed in a cell.

DESCRIPTION OF SPECIFIC EMBODIMENTS

The detection system of the present invention comprises a non-infectious viral particle, a reporter group, and a linking molecule which is capable of linking the viral particle to an analyte of interest. The viral particle used in the present invention preferably is a noninfectious viral particle, more preferably a non-infectious bacteriophage particle, such as a non-infectious particle from a bacteriophage of the T4 Even family, and most preferably a Bacteriophage T4 capsid. The reporter group may be any molecule which can be detected by a detection means, such as light microscopy or fluorescence microscopy. In a preferred embodiment, the reporter group comprises a fluorescent protein enclosed in the cavity of the viral particle. The linking molecule may be a fusion protein comprising an outer capsid protein and an extra polypeptide. The linking molecule is capable of linking the viral particle to the target analyte of interest, either via covalent interactions or non-covalent interactions, or both. For example, the extra polypeptide may be a single chain Fv molecule which directly binds to the target analyte of interest. The extra polypeptide may also indirectly bind to the target analyte via another molecule, for example, via a bivalent protein which can simultaneously bind to the extra polypeptide and the target analyte.

The reporter group and the linking molecule preferably are not components of a naturally occurring virus. In one embodiment, the reporter group and/or the linking molecule are exogenous to the viral particle, and are synthesized and/or prepared separate from the viral particle. For example, the reporter group and/or the linking molecule may be assembled or linked to the viral particle after the viral particle has been isolated from cells in which the viral particle is expressed and assembled. The reporter group and/or the linking molecule may be linked to the viral particle out of cells or in a cell free system.

As used herein, a "detection system" means an isolated system which is capable of binding to an analyte of interest. A detection system is capable of "recognizing" an analyte if the system is capable of binding to the analyte.

An "analyte" means any object of interest. For example, an analyte may be a molecule, a chemical compound, a protein, a polynucleotide, a lipid, a polysaccharide, a cell, a component of a cell, or a tissue.

A "reporter group" is a molecule which is capable of being detected by a detection means. A reporter group includes, but is not limited to, a radioactive or fluorescent chemical compound, an antibody, a fluorescent protein, a protein conjugated with a radioactive or fluorescent chemical compound, a protein or chemical compound which binds to another radioactive or fluorescent protein or chemical compound.

A "linking molecule" is a molecule which is capable of linking two object together. For example, a linking molecule may be a bivalent antibody fragment or a single chain Fv molecule which can non-covalently bind to two different objects simultaneously.

An object is "linked" to another object if the two objects associate with each other via either non-covalent interactions or covalent interactions, or via both types of interactions. As used herein, non-covalent interactions include the physical restrains imposed by a viral capsid to a molecule enclosed therein.

A first protein "comprising" a second protein means that the first protein comprises the amino acid sequence of the second protein.

An "outer capsid protein" is a naturally occurring protein which is located at the exterior surface of a viral capsid.

A "non-essential outer capsid protein" is an "outer capsid protein" expression of which is not required for the viability of a virus. A virus may be either a naturally occurring virus or a virus which has been intentionally modified by humans.

A component is "exogenous" to a viral particle if the component is not a component of the virus from which the viral particle is derived. A component of a virus is a component which is encoded by the genome of said virus and can be expressed therefrom. Said genome can be either naturally occurring, or has been intentionally modified by human in the laboratory.

The term "naturally occurring," as applied to an object, refers to the fact that the object can be found in nature. For example, a polypeptide or polynucleotide that is present in an organism, including a virus or a viral particle, is "naturally occurring" if the organism can be isolated from a source in nature and has not been intentionally modified by man in the laboratory.

As used herein, a viral particle is the physical embodiment of a virus or part thereof, and is said to be "derived" from said virus. A viral particle preferably comprises a viral capsid which may be either naturally occurring or has been intentionally modified by man in the laboratory. A viral capsid, as used herein, may or may not contain the nucleic acid material of the virus from which the capsid is derived.

A "non-infectious" viral particle is a viral particle which is incapable of infecting host cells upon contacting said host cells under normal conditions. Normal conditions are conditions under which the host cells are maintained in nature or in the laboratory. A viral particle is capable of infecting a host cell if the particle can enter the host cell and produce a copy thereof. A non-infectious bacteriophage particle is incapable of forming plaques when being plated on its bacterial host.

A protein is "enclosed" in a viral particle if the protein is located in the cavity of the viral capsid of the viral particle.

Viral Particle

A viral particle from any type of virus, preferably a bacterial virus or bacteriophage, may be used to construct the detection system of the present invention. The viral particle preferably is non-infectious, thus reducing potential health hazards associated with using infectious viruses. When a bacteriophage particle is used, it preferably is from a bacteriophage of the T Even family. More preferably, the bacteriophage particle is a mutant which has only a capsid and does not have a tail structure. Most preferably, the bacteriophage particle is a T4 capsid. A bacteriophage particle without a tail structure may reduce non-specific binding, and thus enhance the sensitivity of detection.

A Bacteriophage T4 mutant which consists of only a capsid after completion of assembly is preferably used. Bacteriophage T4 capsid has a size of about 65×95 nm, which is too small to be visible in light microscopes. The Bacteriophage T4 capsid is usually attached to a contractile tail. Normally, the capsid and tail are independently assembled inside a suitable bacteria and then combined. Numerous mutants are readily available that allow one to make complete capsids without tails.

A bacteriophage capsid may comprise several non-essential outer capsid proteins, deletion of which does not significantly affect the viability of the bacteriophage. For example, hoc and soc proteins of Bacteriophage T4 are two non-essential outer capsid proteins which are inserted into multiple sites on the exterior surface of the Bacteriophage T4 capsid. Normally, the exterior surface of a Bacteriophage T4 capsid comprises about 160 copies of hoc protein and about 960 copies of soc protein. Both proteins may be added and incorporated into a T4 capsid after the capsid has been assembled without both proteins. Hoc and soc protein can associate tightly with the capsid surface upon incorporation. See, for example, Black, L. W., Showe, M. K. and Steven, A. C. (1994), Molecular Biology of Bacteriophage T4 (ed. by J. D. Karam, ASM Press), pages 218–258, which is hereby incorporated by reference.

In one embodiment, the detection system may comprise at least two viral particles, preferably two bacteriophage particles, more preferably two Bacteriophage T4 capsids without the tail structures. The two viral particles are preferably linked via outer capsid proteins. For example, an outer capsid protein of one viral particle may be covalently linked to an outer capsid protein of the other viral particle. Linkers capable of cross linking proteins may also be suitable for linking the outer capsid proteins of two viruses. For suitable linkers, see U.S. Pat. No. 5,262,524, U.S. Pat. No. 5,091,542, and Landsdorp, et al., "Cyclic Tetramolecular Complexes Of Monoclonal Antibodies: A New Type Of Cross-linking Agent," Euro. J. Immunol., 16:679–83 (1986). These references are hereby incorporated by reference.

Reporter Group

A reporter group may be any molecule which can give rise to a detectable signal. It may be, or preferably may not be, a component of a naturally occurring virus. For example, it may be a fluorescent compound, such as fluorescein or R-phycoerythrin, or a radioactive compound, which is linked, preferably covalently linked, to an outer capsid protein of the virus. A reporter group may also be a ligand which can bind to a detectable receptor, for example, a fluorescein-conjugated antibody, and the ligand may be linked, preferably covalently, to an outer capsid protein of the viral particle.

Methods for linking a chemical compound to a protein are well known in the art. For instance, a chemical compound may be covalently linked to a protein via the side chains of the amino acid residues of the protein. Suitable side chains include amine, carboxyl, phenyl, thiol or hydroxyl groups. A chemical compound may also be covalently linked to a protein via a linker. Various conventional linkers are well known, for example, disiocyanates, diisothiocyanates, bis (hydroxysuccinimide) esters, carbodiimides, maleimide-hydroxysuccinimide esters, and glutaraldehyde.

In addition, a chemical compound may be non-covalently linked to a viral capsid. For example, a chemical compound may bind to a fusion protein comprising a hoc protein and a single chain Fv molecule which specifically recognizes the chemical compound. The fusion protein is incorporated into the viral capsid via the portion consisting of hoc protein.

Preferably, a reporter chemical compound may be linked to an outer capsid protein of the virus after completion of the assembly of the virus. For example, a mutant virus whose capsid lacks a particular type of non-essential outer capsid protein may be used. First, a chemical compound may be conjugated to the non-essential outer capsid protein, and then, the conjugated non-essential outer capsid protein may be incorporated, preferably out of cells, into an assembled capsid of said virus. Preferably, conjugation of the chemical compound to a non-essential outer capsid protein does not significantly affect the ability of the outer capsid protein to be incorporated into the viral capsid. The ability of the modified outer capsid protein to be incorporated into a capsid can be easily tested by evaluating whether the final capsid has the reporter chemical compounds. In one embodiment, a reporter chemical compound is preferably linked to a viral capsid after the linking molecule, which is capable of linking the viral capsid to the target analyte of interest, has been incorporated into the viral capsid.

Where a non-essential outer capsid protein has multiple incorporation sites on a viral capsid, multiple copies of reporter group may be incorporated into the capsid. For example, soc and hoc protein are non-essential outer capsid protein of Bacteriophage T4. Soc and hoc protein have about 960 and 160 incorporation sites on a T4 capsid, respectively. T4 mutants which lack either soc or hoc protein are available. See, for example, Ishii, T and Yanagida, M. (1977), J. Mol. Biol. 109:487–514, which is herein incorporated by reference. T4 mutants which lack both hoc and soc protein are also available or can be prepared by standard phage cross techniques. See id. A reporter chemical compound may be linked to either soc or hoc protein using methods as appreciated by one of skill in the art. The soc or hoc protein thus modified may then be incorporated into the capsid of the T4 mutant which lacks soc or hoc protein. By this means, at least about 960 reporter chemical compounds may be incorporated into a T4 capsid via soc proteins, and at least about 160 reporter chemical compounds may be incorporated via hoc proteins. Because each soc or hoc protein may be linked to more than one reporter compound, the total number of incorporated reporter chemical compounds may be well above 960 or 160, respectively. Moreover, by changing the relative concentration between the mutant T4 capsid and the modified non-essential outer protein, one of skill in the art may link various numbers of the reporter chemical compound to the T4 capsid. For instance, the number of reporter chemical compounds that can be attached to a mutant T4 capsid via soc protein may range, for example, from zero to at least about 50, or to at least about 100, or to at least about 200, or to at least about 960.

In another embodiment, the reporter group may be a fusion protein comprising an outer capsid protein covalently linked to an extra amino acid sequence which preferably is a fluorescent protein. The outer capsid protein preferably is a non-essential outer capsid protein. The fusion protein preferably is incorporated into a capsid after completion of the assembly of the viral capsid, for example, the incorporation may be performed after the viral capsid has been isolated from cells in which it is assembled. More preferably, the fusion protein is incorporated after the linking molecule, which is capable of linking the capsid to an analyte of interest, has been incorporated into the viral capsid. In a preferred embodiment, the virus is a T4 mutant which lacks hoc or soc protein, and the fusion protein comprises hoc or soc protein, respectively. In a more preferred embodiment, the T4 mutant further lacks the tail structure. Where an outer capsid protein, preferably a non-essential outer capsid protein, has multiple incorporation sites on a viral capsid, multiple copies of a fusion protein comprising a fluorescent protein and the outer capsid protein may be incorporated into the viral capsid.

In a preferred embodiment, the reporter group comprises a fluorescent protein which is enclosed within the viral capsid. A fluorescent protein can emit light at a detectable wavelength, preferably at a visible wavelength, upon being excited at another wavelength. There are several suitable, commercially available fluorescent proteins with different excitation and emission properties. For example, red fluorescent protein, cyan fluorescent protein, yellow-green fluorescent protein, green fluorescent protein and blue fluorescent protein are commercially available from Clontech. More preferably, the Green Fluorescent Protein isolated from jellyfish *Aequorea Victoria* may be used.

A capsid targeting sequence (CTS) may be added to the N-terminus of a fluorescent protein. A CTS is a sequence with which a protein is capable of being located into the cavity of a viral capsid during assembly of the capsid. In Bacteriophage T4, the preferred CTS consists of ten amino acid residues, having the amino acid sequence Met-Lys-Thr-Tyr-Gln-Glu-Phe-Ile-Ala-Glu. It has been shown that an average of about 200 Green Fluorescent Proteins from jellyfish *Aequorea Victoria*, fused with the CTS sequence, can be targeted into a single T4 capsid. See Mullaney, J. M. and Black, L. W. (1998), *J. Mol. Biol.*, 283:913–929, which is hereby incorporated by reference.

Linking Molecule

The linking molecule is capable of linking the viral particle to a target analyte of interest. A suitable linking molecule may be any kind of molecule, including, but not being limited to, a chemical compound which is linked to the virus and is capable of binding to, or cross linking, the target analyte of interest. A suitable linking molecule may also be an antibody, a fragment of an antibody such as the Fab fragment of an antibody, or a single chain Fv molecule. A chemical compound may be linked to an outer capsid protein via traditional means as appreciated by one of skill in the art. Preferably, a chemical compound is linked to a non-essential outer capsid protein, and then incorporated into a viral capsid after completion of the assembly of the capsid. For example, incorporation may be performed after the capsid has been isolated from cells from which it is assembled. More preferably, the nonessential outer capsid protein is hoc or soc protein of Bacteriophage T4, and the viral particle is a mutant Bacteriophage T4 capsid which lacks hoc or soc protein. Most preferably, the mutant T4 capsid lacks a tail structure.

In a preferred embodiment, the linking molecule may be a fusion protein comprising an outer capsid protein and an extra amino acid sequence. Preferably, the outer capsid protein is a non-essential outer capsid protein, and the extra amino acid sequence is a single chain Fv molecule specific to the target analyte. More preferably, the viral particle is a mutant Bacteriophage T4 capsid which lacks said nonessential outer capsid protein. A preferred nonessential outer capsid protein is either hoc or soc protein of Bacteriophage T4. Most preferably, the mutant T4 capsid lacks the tail structure. It has been shown that hoc or soc proteins can be fused with other polypeptides and that these fusion proteins can be attached to T4 capsids. See Ren, Z. J., Baumann, R. G. and Black, L. W. (1997), *Gene* 195:303–311; Ren, Z. J., Lewis, G. K., Wingfield, P. T., Locke, E. G., Steven, A. L. and Black, L. W. (1996), *Protein Science* 5:1833–1843; Ren, Z. J. and Black, L. W. (1998), *Gene* 215: 439–444; Jiang, J., Abu-Shilbayeh, L. and Rao, V. B. (1997), *Infection and Immunity* 65: 4770–4777. These references are hereby incorporated by reference. Thus, a capsid lacking hoc or soc protein offers about 160 or 960 sites, respectively, for incorporation of fused linking molecules.

A single chain Fv molecule (scFv) has been described in U.S. Pat. No. 4,704,692, U.S. Pat. No. 4,946,778, R. Raag and M. Whitlow, "Single Chain Fvs. " FASEB Vol 9:73–80 (1995) and R. E. Bird and B. W. Walker, "*Single Chain Antibody Variable Regions*," TIBTECH, Vol 9: 132–137 (1991). These references are incorporated herein by reference. A single chain Fv molecule usually comprises a variable region of an antibody light chain and a variable region of an antibody heavy chain. The two variable regions are covalently linked by a peptide linker, and form a target binding site. Construction of a scFv molecule is disclosed, for example, in European Patent Application No. 239400, U.S. Pat. No. 4,946,778, and R. E. Bird and B. W. Walker, Single Chain Antibody Variable Regions, *TIBTECH*, Vol 9: 132–137 (1991). These references are hereby incorporated by reference.

A single chain Fv molecule may be made by fusing an antibody's light chain variable region with its heavy chain variable region via a peptide linker. Variable regions of antibodies may be derived by immunizing an appropriate vertebrate, normally a domestic animal, and most conveniently a mouse. The immunogen will be the target analyte of interest, or where a hapten is of interest, an antigenic conjugate of the hapten to an antigen such as keyhole limpet hemocyanin (KLH). The immunization may be carried out conventionally with one or more repeated injections of the immunogen into the host mammal, normally at two to three week intervals. Usually three days after the last challenge, the spleen is removed and dissociated into single cells to be used for cell fusion to provide hybridomas from which mRNA can readily be obtained by standard procedures known in the art. DNA sequences may be obtained through reverse transcription of the mRNAs. The above procedures can produce an antibody specific to almost any immunogenic target analyte of interest. The DNA sequences coding for the variable regions of the thus produced antibody may be used for construction of a single chain Fv molecule.

Variable regions of antibodies may also be obtained using M13 bacteriophage display. See Burton et al, *Adv. Immuno.* 57:191–280 (1994). Essentially, a cDNA library for antibodies is generated from mRNA obtained from a population of antibody-producing cells, such as B-lymphocytes. Amplified cDNAs are cloned into M13 phage display vectors creating a library of phage which expresses the antibody fragments on the surface of phages. Phages which display the antibody fragment of interest are selected using the affinity to the antigen. The selected phages are amplified to produce the antibody of interest, which may be used for construction of a single chain Fv molecule.

In another embodiment, an antibody or a single chain Fv molecule specific to an analyte of interest may be linked to an outer capsid protein via chemical means as appreciated by one of skill in the art, for example,.using protein-protein cross linkers. Conjugation of an antibody or a single chain Fv molecule to another protein preferably may not significantly affect the binding specificity and affinity of the antibody or scFv molecule and the ability of the outer capsid protein to be stably associated with the viral capsid. The binding specificity and affinity of a antibody or scFv molecule thus modified, and the ability of the outer capsid protein to stably associate with the viral capsid, may be evaluated by testing whether the viral particle is able to bind to the analyte of interest.

Where both the reporter group and the linking molecule are linked to outer capsid proteins, the outer capsid protein used for conjugating the linking molecule preferably is different from the outer capsid protein that is used for conjugation of the reporter group. For example, when a Bacteriophage T4 mutant which lacks both hoc and soc proteins is used, the linking molecule may be linked to the hoc protein while the reporter group may be linked to the soc protein.

The present invention will be understood more readily by reference to the following examples, which are provided by way of illustration and are not intended to be limiting of the present invention.

EXAMPLE 1

Preparation of a Mutant Bacteriophage T4 Capsid Lacking Hoc and Soc Proteins

A T4 mutant (T4-soc) whose capsid lacks soc protein is prepared, and a second T4 mutant (T4-hoc) whose capsid lacks hoc protein is also prepared. See Ishii, T and Yanagida, M. (1977), *J. Mol. Biol.* 109:487–514. A third T4 mutant (T4-soc-hoc) which lacks both hoc and soc proteins is made by crossing T4-soc and T4-hoc using standard phage crossing techniques. See, for example, Carlson, K. and Miller, E. S. (1994), Molecular Biology of Bacteriophage T4 (ed. By J. D. Karam, ASM Press), pages 438–460, which is incorporated herein by reference.

A T4 mutant (T4+GFP) whose capsid encloses multiple copies of Green Fluorescent Protein (GFP) is prepared. See Mullaney, J. M. and Black, L. W. (1998), *J. Mol. Biol.*, 283:913–929. Crossing T4+GFP with T4-soc-hoc creates another T4 mutant (T4+GFP-soc-hoc) which lacks soc and hoc proteins but has GFP enclosed in its capsid.

A T4 mutant (T4capsid) with an amber mutation (amberE18) in gene 18 is further prepared. See Carlson, K. and Miller, E. S., supra. This mutant has the tail structure, thus being infectious, when grown in a suppressing host cell, such as *E. coli* stain CR63. However, this mutant loses the tail structure, thus being non-infectious, when grown in a non suppressing host cell, such as *E. coli* strain B.

Crossing T4capsid with T4+GFP-soc-hoc in a suppressing host cell, such as *E. coli* stain CR63, generates a T4 mutant (T4capsid+GFP-soc-hoc) which possesses the mutation features of both T4capsid and T4+GFP-soc-hoc. T4capsid+GFP-soc-hoc stock is prepared in a suppressing host cell, such as *E. coli* stain CR63. A thus prepared T4capsid+GFP-soc-hoc has the tail structure and enclosed GFP, but lacks soc and hoc protein in its capsid. This T4capsid+GFP-soc-hoc is then used to infect a non suppressing host cell, such as *E. Coli* strain B, from which a T4 capsid lacking the tail structure and soc and hoc proteins is produced. This T4 capsid encloses multiple copies of GFP.

The T4 capsids with GFP are concentrated by centrifuging the lysate of the infected non-suppressing host cells in a 5–20% sucrose gradient. The fast moving capsids, with a sedimentation value of approximately 1,200 S, are collected in a concentrated form.

EXAMPLE 2

Detection of a Nucleic Acid Molecule

In this example, we describes how to employ the disclosed detection system to detect nucleic acid targets. It is to be understood that many variations of how to perform this type of detection are possible. It is also to be understood that other types of fusion proteins would enable the detection of other types of target molecules.

Type II DNA methyltransferases (Mtases) transfers a methyl group to a cytosine or adenine base residue in a double stranded DNA sequence. A DNA Mtase can either stably or covalently bind to a target DNA sequence under appropriate conditions. For example, if the C5 position of a cytosine base carries a fluorine instead of a hydrogen, certain DNA Mtases can remain permanently and covalently attached to the cytosine upon binding. For another example, the DNA Mtase may stably associate with a target DNA sequence if one uses an analogue of the normal cofactor S-adenosylmethionine (SAM), Sinefungin, or a DNA comprising 5-azacytosine (a cytosine analogue). A stable Mtase-DNA complex may also be formed if the target sequence comprises a mismatched cytosine or if one uses a suitable mutant Mtase.

A fusion protein comprising a DNA Mtase covalently linked to a hoc protein of Bacteriophage T4 is prepared. A T4 capsid which encloses multiple copies of GFP and lacks hoc protein is prepared. See Example 1, T4capsid+GFP-soc-hoc. A peptide tag comprising six histidine residues is further fused to the fusion protein. The resultant fusion protein is expressed and purified by standard methods, including affinity chromatography using a nickel column. The fusion protein is then mixed with and incorporated into the T4 capsid to make a detection system which is capable of detecting a DNA sequence comprising the normal recognition sequence, or the normal recognition sequence where the target cytosine is replaced by a 5-flurocytosine or by 5-azacytosine or where there is a mismatch at the target cytosine.

EXAMPLE 3

Detection of a Protein

The cDNA sequence encoding a single chain Fv molecule (scFv) which can specifically bind to the target protein is prepared as appreciated by one of skill in the art. The scFv molecule is then fused to a hoc protein of Bacteriophage T4. A peptide tag comprising six histidine residues is further fused to the fusion protein. The final fusion protein is expressed and purified by standard methods, including affinity chromatography using a nickel column. A T4 capsid which encloses multiple copies of GFP and lacks hoc protein is prepared. See Example 1, T4capsid+GFP-soc-hoc. The purified fusion protein is then mixed with and incorporated into the T4 capsid to make a detection system which is capable of detecting the target protein.

EXAMPLE 4

Detection of a Lipid Molecule

Annexin V specifically recognize phosphatidylserine. Phosphatidylserine is confined to the cytoplasmic side of cellular membranes in normal cells, but becomes inverted and exposed to the exterior of the cell during apoptosis. A fusion protein comprising Annexin linked to a hoc protein of Bacteriophage T4 is prepared. A peptide tag comprising six histidine residues is further fused to the fusion protein. The final fusion protein is expressed and purified by standard methods, including affinity chromatography using a nickel column. A T4 capsid which encloses multiple copies of GFP and lacks hoc protein is prepared. See Example 1, T4capsid+GFP-soc-hoc. The purified fusion protein is then mixed with and incorporated into the T4 capsid to make a detection system which is capable of detecting phosphatidylserine in a cell under apoptosis.

EXAMPLE 5

A Detection System With Two Different Types of Reporter Groups

A T4 capsid which encloses multiple copies of GFP and lacks both soc and hoc proteins is prepared. See Example 1, T4capsid+GFP-soc-hoc. A fusion protein comprising a scFv molecule covalently linked to a hoc protein is prepared. The scFv molecule can bind to the analyte of interest of interest. The scFv-hoc fusion protein is mixed with and incorporated into the T4 capsid.

A fusion protein comprising a soc protein covalently linked to a detectable protein is prepared. The detectable protein may be a fluorescent protein other than GFP, an enzyme such as alkaline phosphatase and luciferase, or a peptide tag such as FLAG-tag which can be detected by a fluorescently labeled antibody. The fusion protein is then mixed with and incorporated into the T4 capsid which has already incorporated the scFv-hoc fusion protein. Thus, the resultant T4 capsid comprises two types of reporter groups: one is the fluorescent protein enclosed inside the T4 capsid, the other is the fusion protein which comprises a soc protein and a detectable protein and is located at the exterior surface of the capsid.

I claim:

1. A system for detecting an analyte comprising a non-infectious bacteriophage particle from the T Even family, a reporter group linked to said bacteriophage particle, and a linking molecule which links said bacteriophage particle to said analyte, wherein said reporter group and said linking molecule are not components of a naturally occurring virus.

2. The system of claim 1, wherein said bacteriophage particle from the T Even family comprises a capsid and does not have a tail structure.

3. The system of claim 2, wherein said capsid is a Bacteriophage T4 capsid.

4. The system of claim 3, comprising at least 50 reporter groups.

5. The system of claim 3, comprising at least 100 reporter groups.

6. The system of claim 3, comprising at least 200 reporter groups.

7. The system of claim 3, wherein said reporter group comprises a fluorescent molecule.

8. The system of claim 7, wherein said fluorescent molecule comprises a fluorescent protein.

9. The system of claim 8, wherein said fluorescent protein is enclosed within said Bacteriophage T4 capsid.

10. The system of claim 9, wherein said fluorescent protein is a green fluorescent protein.

11. The system of claim 10, wherein said green fluorescent protein comprises the green fluorescent protein of jellyfish *Aequorea victoria*.

12. The system of claim 7, wherein said reporter group further comprises an outer capsid protein covalently linked to said fluorescent protein.

13. The system of claim 12, wherein said outer capsid protein of said reporter molecule being a non-essential outer capsid protein.

14. The system of claim 13, wherein said non-essential outer capsid protein is selected from the group consisting of hoc and soc protein of Bacteriophage T4.

15. The system of claim 14, wherein said linking molecule comprises an outer capsid protein covalently linked to an extra amino acid sequence.

16. The system of claim 15, wherein said outer capsid protein of said linking molecule is a non-essential outer capsid protein.

17. The system of claim 16, wherein said non-essential outer capsid protein of said linking molecule is selected from the group consisting of hoc and soc protein of Bacteriophage T4.

18. The system of claim 17, wherein said non-essential outer capsid protein of said linking molecule and said non-essential outer capsid protein of said reporter molecule are not identical.

19. The system of claim 17, wherein said extra amino acid sequence comprises a polypeptide selected from the group consisting of a single chain Fv molecule, an Annexin and a DNA methyltransferase.

20. The system of claim 7, wherein said linking molecule comprises an outer capsid protein covalently linked to an extra amino acid sequence.

21. The system of claim 20, wherein said outer capsid protein of said linking molecule is a non-essential outer capsid protein.

22. The system of claim 21, wherein said non-essential outer capsid protein of said linking molecule is selected from the group consisting of hoc and soc protein of Bacteriophage T4.

23. The system of claim 1, further comprising at least two bacteriophage particles which are linked together, either covalently or non-covalently.

24. A system for detecting an analyte comprising a non-infectious bacteriophage particle from the T Even family, a reporter group linked to said bacteriophage particle, said resporter group comprising a first outer capsid protein covalently linked to a first extra amino acid sequence, and a linking molecule which links said bacteriophage particle to said analyte, said linking molecule comprising a second outer capsid protein covalently linked to a second extra amino acid sequence; wherein said reporter group and said linking molecule are not components of a naturally occurring virus and wherein said first and second extra amino acid sequence are not identical.

25. The system of claim 24, wherein said first and second outer capsid proteins are non-essential outer capsid proteins.

26. The system of claim 25, wherein said non-infectious bacteriophage particle from the T Even family does not have a tail structure.

27. The system of claim 26, wherein said first outer capsid protein is selected from the group consisting of soc and hoc protein of Bacteriophage T4, and said second outer capsid protein is selected from the group consisting of soc and hoc protein of Bacteriophage T4.

28. The system of claim 27, wherein said first extra amino acid sequence comprises a fluorescent protein.

29. The system of claim 28, wherein said second extra amino acid sequence comprises a polypeptide selected from the group consisting of a single chain Fv molecule, an Annexin and a DNA methyltransferase.

30. A method of making a system for detecting an analyte, comprising assembling
   a. a non-infectious bacteriophage particle from the T Even family;
   b. a reporter group, said reporter group comprising a first outer capsid protein;
   c. a linking molecule which links said bacteriophage particle to said analyte, said linking molecule comprising a second outer capsid protein;

wherein said reporter group and said linking molecule are not components of a naturally occurring virus.

31. The method of claim 30, wherein said bacteriophage particle does not have a tail structure.

32. The method of claim 31, wherein said first outer capsid protein is covalently linked to a first extra amino acid sequence.

33. The method of claim 32, wherein said second outer capsid protein is covalently linked to a second extra amino acid sequence.

34. The method of claim 33, wherein said first outer capsid protein is selected from the group consisting of soc and hoc protein of Bacteriophage T4, and said second outer capsid protein is selected from the group consisting of soc and hoc protein of Bacteriophage T4.

* * * * *